United States Patent [19]

Sandine et al.

[11] Patent Number: 4,766,076
[45] Date of Patent: Aug. 23, 1988

[54] METHOD AND BUFFERED BULK STARTER MEDIA FOR PROPAGATION OF USEFUL BACTERIA

[75] Inventors: William E. Sandine; James W. Ayres, both of Corvallis, Oreg.

[73] Assignee: The State of Oregon acting by and through the Oregon State Board of Higher Education on behalf of Oregon State University, Eugene, Oreg.

[21] Appl. No.: 622,112

[22] Filed: Jun. 19, 1984

[51] Int. Cl.$^4$ .................. C12N 1/20; C12R 1/225; C12R 1/46; A23C 19/032
[52] U.S. Cl. .................. 435/253; 435/853; 435/885; 426/43; 426/61; 426/583
[58] Field of Search .............. 435/253, 853, 854, 855, 435/856, 857, 885; 426/36, 43, 583, 41, 34, 61

[56] References Cited

U.S. PATENT DOCUMENTS

| | | | |
|---|---|---|---|
| 3,887,641 | 6/1975 | Tsuchiya | 260/845 |
| 3,897,307 | 7/1975 | Porubcan et al. | 426/61 |
| 4,282,317 | 8/1981 | Roth | 435/253 |

OTHER PUBLICATIONS

Merck Index, Eighth Ed., 1968, p. 196.

*Primary Examiner*—Elizabeth Weimar
*Attorney, Agent, or Firm*—Klarquist, Sparkman, Campbell, Leigh & Whinston

[57] ABSTRACT

The invention comprises a novel starter medium for the commercial propagation of acid producing bacteria, such as those used in food fermentation processes. The compositions are unique in that they contain a highly effective buffering ingredient which is a sodium, potassium, or ammonium salt or double salt of a linear aliphatic dibasic acid having from three to seven carbon atoms. The salts are present in an amount sufficient to maintain the growth medium at pH levels of about 5.0 or above during the time in which the bacteria are multiplying in the culture medium. Disodium or diammonium succinate, glutarate, or adipate are materials which have been found to be particularly effective. These may be used in combination with nutrients such as whey, whey permeate, nonfat dried milk, yeast extract, and diammonium phosphate. The addition of trace quantities of certain metals promotes the growth and activity of the acid producing bacteria. Small quantities of ferrous, manganous, or manganese ions are particularly useful. A combination of iron and manganese with the other ingredients in the media produced results better than either of these materials standing by itself. In a commercial test, the cheese produced using an inoculant based on one of the present formulations was of excellent quality. Most of the formulations containing the bibasic acid salts appear to be highly resistant to bacteriophage infection.

29 Claims, No Drawings

METHOD AND BUFFERED BULK STARTER MEDIA FOR PROPAGATION OF USEFUL BACTERIA

BACKGROUND OF THE INVENTION

The present invention comprises an improved family of bulk starter media and the use of these media for propagation of useful acid producing bacteria. The products and process of the invention are particularly beneficial in producing bacterial cultures for fermentation processes in the food industry.

Many important food products are prepared by deliberate controlled bacterial fermentation. Among these can be mentioned the many products of milk fermentation such as hard and soft cheeses, cottage cheese, and yogurt. Many types of pickles and sausages are also dependent upon bacterial fermentation for proper texture and flavor development. Cheddar cheese production can be cited as exemplary of the many food fermentation processes. In its commercial production, large vats of milk are treated with an enzyme, such as rennett, in order to induce clotting. Additionally, the milk is inoculated with cultures of lactic acid producing bacteria to provide the required acidic conditions, as well as the desired flavor, texture, and odor characteristics of the cheese. These bacteria act mainly upon lactose and similar carbohydrate materials and produce increasing quantities of lactic acid as the fermentation proceeds. While there are a great many species and strains of lactic acid producing bacteria, relatively few have assumed commercial importance. Among these can be included *Streptococcus cremoris, S. lactis, S. thermophilus, S. diacetylactis,* and *Lactobacillus bulgaricus.*

The bacterial cultures which are added to the milk are generally propagated at the dairy or cheese plant from selected pure strains of the bacteria available commercially from a number of sources well known within the industry. These starter bacteria are normally sold and maintained in frozen condition so that their activity can be preserved for long periods of time. When required for use, the starter bacteria are added to a growth medium, generally called a bulk starter medium, which contains essential mineral and organic nutrients which are known from experience to be required for the particular species being propagated. In particular, the bulk starter must contain energy materials, usually sugars and similar readily metabolized carbohydrates, and a suitable source of nitrogen. Very often a source of phosphorus is also required. Growth media are normally supplied as a dry granular mixture. This is dissolved or suspended in water and pasteurized to destroy any ambient pathogens. It is then cooled and inoculated with the bacteria to be propagated. The culture thus produced is maintained at slightly elevated temperature for a period of time sufficient to allow the growth of about $10^6$ to $10^8$ colony forming units or cells (cfu) per ml. In many cheese plants, it is convenient to incubate the starter culture overnight. This will then be used the next morning for cheese production.

One problem which frequently besets bacterial fermentations is infection with bacteriophages. Each of the major strains of cheese producing bacteria also appears to have a specific bacteriophage (or simply phage) which has evolved as a homologous antagonist. In response to this problem, food scientists have developed culture or starter media which are phage-inhibitory. Gulstrom and coworkers, *J. Dairy Sci.,* 62:208–221 (1979), have evaluated eight commercially available phage-inhibitory starter media using a large number of different bacterial strains and phages. The most effective of the group of media evaluated appear to be those having phosphate-citrate buffer systems. Gulstrom et al. point out that available calcium ion is an essential for phage propagation. A response to this knowledge has been the formulation of low calcium starter media, or media which contain materials such as orthophosphate salts or other materials which bind calcium and make it unavailable. Citrate buffers are also known to be effective.

Unfortunately, many media which offer good phage control are not particularly good for nourishing the desired bacteria. Gulstrom et al. point out that in a medium, the ability to support good bacteria growth and at the same time suppress phage proliferation are mutually exclusive properties. Some optimum balance must be sought.

Another ingredient often added to lactic acid starter media is a buffering salt. The initial pH of media for propagation of cheese Streptococcal bacteria is normally in the range of 6.5–6.8. As the bacteria proliferate, the pH drops due to the generation of lactic acid. Below a pH of about 5, bacterial growth slows markedly and the bacteria begin to lose vigor. In actuality, they are being killed or deactivated by the acid they themselves have generated. One widely used commercial system employs a continuous addition of ammonia which serves to neutralize the acid as it is generated. Other systems employ sparingly soluble magnesium compounds, such as magnesium phosphate or magnesium ammonium phosphate, which are solubilized as the pH drops and serve to neutralize a portion of the acid. U.S. Pat. Nos. 4,282,255 and 4,382,965 to Sandine et al. disclose phage-inhibitory media containing magnesium phosphate and/or magnesium ammonium phosphate for acid neutralization. Additionally, they disclose the use of microencapsulated alkaline materials, such as sodium carbonate, which dissolve slowly and serve to give a controlled time release of alkali to the system for acid neutralization. Sinkoff et al., U.S. Pat. No. 4,402,986, describe an aqueous bulk starter medium containing magnesium ammonium phosphate hexahydrate as a neutralizing agent.

One of the problems of starter media containing insoluble or sparingly soluble inorganic compounds is the fact that many of them require agitation during the entire incubation time of the starter media in order to maintain these materials in suspension. Though this requirement for constant agitation is sometimes regarded as a nuisance, it can also be undesirable if it causes excessive oxygenation of the culture. Excessive oxygen tends to retard and inhibit bacterial growth.

Some workers have found that particular metal ions in trace quantities enhance bacterial growth. Etchells et al., U.S. Pat. No. 3,410,755, and Canadian Pat. No. 1,024,393 each disclose the addition of small quantities of magnesium, manganese, and ferrous ions in bacterial growth media.

Despite the commercial availability of several excellent bulk starter media, none to date has proved ideal for the cheesemaker. Continuous ammonia addition requires exceedingly careful attention and control. Some media which have shown excellent properties of phage inhibition often produce cultures of low activity. The present inventors have recognized these problems and have now developed a family of bulk starter media which overcome most of them. The media produced by the teachings of the present invention are phage-inhibitory, do not require continuous agitation, and are internally buffered so that bacterial growth is not inihibited by excessive acid production.

SUMMARY OF THE INVENTION

The present invention comprises dry, granular, later soluble or water dispersable growth media compositions useful to form aqueous growth media for the propagation of acid producing bacteria. The method further comprises the use of these compositions for the propagation and multiplication of such bacteria for use as inoculants in fermentation processes. The compositions of the invention are comprised of a nutrient mixture which supplies the essential carbohydrate, nitrogen, and other nutrients necessary for the growth of the particular strain of bacteria being propagated. A novel element of the compositions is the inclusion of a water soluble, nontoxic buffering agent which is selected from any of the sodium, potassium, or ammonium salts and double salts of linear aliphatic dibasic acids having from three to seven carbon atoms. The buffering agent is present in an amount sufficient to provide an aqueous growth medium with an initial pH from about 5.5 to 7.5 and to buffer the growth medium to pH levels which will not drop below about 5.0 for at least sixteen hours during the time the bacteria are propagating to numbers useful as an inoculant in the fermentation process. Depending on incubation temperature and other factors, the media maintains at not less than pH 5.0 for twenty hours or longer. For best results with a wide spectrum of bacteria, the buffering agent will be present in an amount sufficient to provide an initial pH from about 6.5 to 7.0.

The diammonium or disodium salts of succinic, glutaric, and adipic acids are of particular value in the process. The buffering agents may be added in the form of a salt or double salt of the particular cations chosen. They may also be formed in situ after the growth medium is dissolved or dispersed in water by the inclusion of the dibasic acid along with an alkaline salt of the particular cation chosen. Ihus, if disodium adipate were the buffering agent of choice, either this compound or a mixture of adipic acid and a compound such as sodium carbonate could be included with the other dry materials of the growth medium.

The buffering agents should be present in an amount sufficient for acid neutralization. And, to avoid the need for agitation, the buffering agents should not be present in such a quantity that solids settle out of the aqueous medium. Using the above-mentioned salts of succinic, glutaric, or adipic acids, there should be no settling when the combined amount of salts of the linear aliphatic acids is less than about fifty grams per liter of the aqueous medium. When salts of lower or higher molecular weight acids are used, proportionally smaller or larger amounts may be included.

In general, suitable nutrients for any commercially important species of bacterium are well known. However, in any specific growth medium composition, one or more nutrient materials may be found to be particularly effective. Whether a specific nutrient material is or is not within this category is something that cannot be readily predicted. The media of the present invention, especially when used for the propagation of the various species and strains of Streptococci used for cheese production, can effectively employ dried sweet whey, dried whey permeate, and nonfat dried milk among the nutrient ingredients. Diammonium phosphate and yeast extracts are further desirable ingredients.

For most bacterial strains, further growth enhancement will be noted by the inclusion of trace amounts of a metal ion selected from the group of ferrous, manganous, or magnesium, or mixtures of these materials. By "trace amount" is meant an amount below about 250 ppm (0.025%) in the case of magnesium, and below about 100 ppm in the case of ferrous and manganous ions. Most typically, these ions will be present in amounts below about 25 ppm. In some cases, combinations of these metal ions are more effective than any one of them individually. A composition containing about 10 ppm ferrous ion and 5 ppm manganous ion is as or more effective in enhancing bacterial growth than either of these metal ions by themselves. The amounts just cited of these trace metals are based on the ultimate aqueous solution or dispersion of the dry growth medium and not on the dry medium itself.

The media of the invention are effective when used with any of the commonly employed Streptococcal or Lactobacillus groups of bacteria commonly employed in the food fermentation industries. These bacteria include *Streptococcus cremoris, S. lactis, S. thermophilus, S. diacetylactis,* and *Lactobacillus bulgaricus.*

The use of the novel buffering compounds of the present invention enhances bacterial growth by maintaining pH in the optimum range during the growth period. In most compositions, they further contribute desirable phage-inhibitory properties. Phage inhibitory agents such as nontoxic soluble phosphates and/or nontoxic soluble citrates, may be included to enhance phage inhibition. Other phage inhibitory substances include EDTA and salts of oxalic acid, as described in Kadis and Babel, *J. Dairy Sci.,* 45:486–491 (1962). The aforesaid and similar phage inhibitory substances may be used alone or in combination.

As normally employed, aqueous starter media according to the invention do not require continuous agitation. All that is usually necessary is mild agitation at the beginning and end of the propagation period in order to insure uniform dispersion of all materials and organisms within the inoculant.

It is an object of the present invention to provide a medium which maintains a pH above about 5.0 during fermentation by an acid-producing bacterial culture.

Another object of the invention is to provide a highly effective phage-inhibitory medium for the propagation of acid producing bacteria.

It is also an object to provide a liquid bacterial growth medium which does not require agitation during use, preferably a medium containing a minimum of insoluble substances.

It is a further object of the invention to provide a bacterial growth medium which results in an inoculant having high bacterial counts and in which the bacteria maintain a high degree of activity.

These and many other objects will become readily apparent to one skilled in the art upon reading the following detailed description.

DETAILED DESCRIPTION

It is essential that a good starter or inoculant of a lactic acid generating species should produce lactic acid at a vigorous and steady rate beginning immediately after addition to the material being fermented. In this regard, absolute numbers of bacteria in a given inoculant are not as important as the activity of these bacteria. Many starters will contain large absolute numbers of bacteria, but because of past contact with a medium of low pH, or for other reasons, the bacteria will not react vigorously when added to milk during cheese production. The result is a "slow starter" which has a slow start or lag time and may produce poor quality cheese.

The various starter media described in the following examples show a spectrum of performance. The most preferred compositions, as outlined in the later examples, give outstanding performance, both in their own right and in comparison with the best available commercial starter media. The addition of the sodium, potassium, or ammonium salts or double salts of linear saturated aliphatic dibasic acids in the three to seven carbon atom range has conferred excellent acid control properties to the media, and the combination of ingredients is phage inhibitory. Particularly good phage inhibition is obtained when disodium adipate is present. Only in those formulations containing magnesium phosphate is there evidence that phage inhibition is reduced or lost.

EXAMPLE 1

A bacterial growth medium was prepared by mixing 29 g of whey powder, 4 g of yeast extract, 10 g of diammonium phosphate (DAP), and 12 g of diammonium succinate (DAS) with 800 ml of water. A second medium was prepared which was similar to the above but in which half (6 g) of the DAS was replaced with diammonium adipate (DAA). The media were pasteurized by heating to 85° C. and holding at that temperature for 45 minutes with agitation. Thereafter, the media were cooled to 25° C. Each medium was then inoculated using 0.5 ml of a freshly thawed can of Hansen's commercial starter #57 (Chrs. Hansen's Laboratories, Milwaukie, Wis.). The media were maintained at 25° C. and agitated only during the first and last 15 minutes of bacterial growth.

Activity was measured using a simulated cheddar cheese make procedure beginning with pasteurized milk (NFM-11% solids, w/w). This was inoculated at 1% and 2% by volume with the starter produced above, and held at the following temperatures: 32° C. for 70 min, followed by a slow increase to 39° C. over a 30 min period, followed by a decrease to 38° C., and then holding for 160 min, followed by cooling to 32° C., holding for 40 min, and then measure pH.

The activity was calculated as:

Activity $= (A - B) + (A - C)$ where,

A = uninoculated NFM pH after gradient incubation
B = pH after incubation of NFM inoculated at 1%
C = pH after incubation of NFM inoculated at 2%

Viable cell counts were made on M-17 agar:

| Ingredient | Amount |
| --- | --- |
| Phytone peptone | 5.0 g |
| Yeast Extract | 2.5 g |
| Polypeptone | 5.0 g |
| Beef Extract | 5.0 g |
| Lactose | 5.0 g |
| Ascorbic Acid | 0.5 g |
| Disodium-$\beta$-glycerophosphate | 19.0 g |
| 1.0 M MgSO$_4$.7H$_2$O | 1.0 ml |

-continued

| Ingredient | Amount |
| --- | --- |
| Distilled Water | 1000 ml | pH = 7.0 ± 0.05
Reference: Terzaghi et al., "Improved Medium for Lactic Streptococci and Their Bacteriophage", Appl. Microbiol. 29:807-813 (1975).

After aerobic incubation for 16 hr at 30° C. using a drop-plate technique, activity and viable cell numbers were measured. Results are given in Table I. The pH of the media prior to inoculation and after fermentation are also included.

TABLE I

| | DAS Medium | DAA + DAS Medium |
| --- | --- | --- |
| pH, 0 hr | 6.63 | 6.91 |
| pH, 16 hr | 5.30 | 5.41 |
| Activity, 16 hr | 2.2 | 2.2 |
| cfu/ml*, 16 hr | $1.1 \times 10^9$ | $5.1 \times 10^8$ |

*cfu - viable colony forming units

Thus, partial replacement of DAS with DAA (1:1 ratio) in the DAS medium results in no loss of activity, although the viable cell numbers after 16 hr of growth at 25° C. decreased by about one-half. These results are in the range of those obtained using the best commercially available growth media. Both media maintained pH at a desirably high level.

EXAMPLE 2

A growth medium was prepared as in Example 1 by mixing 29 g of whey powder with 4 g of yeast extract, 12 g of DAS and 10 g of DAP, then suspending this mixture in 800 ml of water. A second medium was prepared using all the above ingredients plus 1.0 g of Mg$_3$(PO$_4$)$_2$. Magnesium phosphate is known to be a bacterial growth enhancer in some media. The media were heated to and held at 85° C. for 45 min with agitation, then cooled to 25° C. and inoculated with 0.5 ml of a freshly thawed can of Hansen's commercial starter #57. Activity and viable cell numbers were measured after 16 hr as described in Example 1; results are given in Table II.

TABLE II

| | DAS Medium without Mg$_3$(PO$_4$)$_2$ | DAS Medium with Mg$_3$(PO$_4$)$_2$ |
| --- | --- | --- |
| Activity at 16 hr | 2.0 | 2.8 |
| cfu/ml at 16 hr | $9.8 \times 10^8$ | $2.7 \times 10^9$ |

Thus, addition of Mg$_3$(PO$_4$)$_2$ improved the growth-promoting ability Of the DAS medium. Similar results were obtained with Hansen's starter #70. This example also shows that high cell numbers of an active culture can be produced in the DAS medium with Mg$_3$(PO$_4$)$_2$ without the continuous or intermittent agitation required for some commercially available media.

EXAMPLE 3

A growth medium was prepared by mixing 29 g of whey powder, with 4 g of yeast extract, 12 g of DAS, 10 g of DAP, and 1 g of Mg$_3$(PO$_4$)$_2$.8H$_2$O, then suspending this mixture in 800 ml of water. A second medium was also prepared in which 12 g of DAA replaced the 12 g of DAS in the medium above. All media were heated to and held at 85° C. for 45 min with agitation, then cooled to 25° C. and inoculated with 0.5 ml of freshly thawed Hansen's commercial starter #57. The media were agitated during the first and last 15 min of growth. Activity and viable cell numbers were measured after about 16¼ hr fermentation as described in Example 1. Initial and final pH of the media were also measured. Results are summarized in Table III.

TABLE III

|  | DAS Medium[b] | DAA Medium[a] |
|---|---|---|
| pH, 0 hr | 6.81 | 6.97 |
| pH, 16 hr | 5.13 | 5.35 |
| Activity, 16 hr | 2.8 | 2.5 |
| cfu/ml, 16 hr | $2.7 \times 10^9$ | $1.9 \times 10^9$ |

[a]Fermentation time 16¼ hr.
[b]Fermentation time 16¼ hr.

Thus, the DAS medium may support activity somewhat better than the DAA medium—i.e., substituting DAA for DAS in a 1:1 ratio results in a slightly decreased activity.

EXAMPLE 4

A growth medium was prepared by mixing 28 g of whey powder with 4 g of yeast extract, 1 g of $Mg_3(PO_4)_2 \cdot 8H_2O$, 15 g of DAP, 12 g of DAS, and 4 g of citric acid, monohydrate, and suspending this mixture in 800 ml of water. Citric acid or its salts are frequently used in combination with phosphates as buffering and bacteriophage control agents in culture media. A second medium was prepared in which 12 g of DAA replaced the DAS in the formulation above. Both media were heated to and held at 85° C. for 45 min with agitation, then cooled to 25° C. and inoculated with 1% ($10^5$ cfu/ml of medium) of *Streptococcus cremoris* HP. This bacterial strain originated in New Zealand and is available at Oregon State University. Agitation was used only for the first and last 15 min of growth. Activity and viable cell numbers were measured following a 16¼ hr fermentation at 25° C. as described in Example 1; media pH values were measured before and after culture growth. Results are given in Table IV.

TABLE IV

|  | DAS Medium | DAA Medium |
|---|---|---|
| pH, 0 hr | 6.52 | 6.66 |
| pH, 16 hr | 4.98 | 5.30 |
| pH, 19 hr | 4.94 | 5.23 |
| Activity, 16¼ hr | 3.0 | 2.7 |
| cfu/ml, 16¼ hr | $3.3 \times 10^9$ | $2.9 \times 10^9$ |

Again, growth in the DAS medium results in a bulk starter a little higher in activity than does growth in the DAA medium, although the amounts are within the range of experimental variation of each other. Note also that the final pH of the DAA medium is higher than that of the DAS medium, indicating more inhibition of acid production in the DAA medium.

EXAMPLE 5

A growth medium was prepared as in Example 4 by mixing 28 g of whey powder with 4 g of yeast extract, 1 g of $Mg_3(PO_4)_2 \cdot 8H_2O$, 12 g of DAS, 15 g of DAP, and 4 g of citric acid, monohydrate, then suspending the mixture in 800 ml of $H_2O$. A second medium was made wherein 28 g of nonfat milk (NFM) powder replaced the whey powder above. Both media were heated to and held at 85° C., cooled, and inoculated with 0.5 ml of a freshly thawed commercial culture (Marschall's MFS or WP). Agitation was discontinued 15 min after adding starter. These cultures are available from Marschall Division of Miles Laboratories, Inc., Madison, Wis. Fermentation continued for 16 hr, agitation was resumed for 15 min, and samples removed for storage at 5° C. and 25° C. and also for 16 hr activity and viable cell counts (as described in Example 1). Stored samples were tested again for activity and cfu/ml of media after one and three days of holdover. For Marschall's culture WP, activity tests and viable cell counts were repeated after 10 days. Results for Marschall's MFS are given in Table V, for Marschall's WP in Table VI.

TABLE V

| Holdover of Culture MFS in DAS Media | | | | | |
|---|---|---|---|---|---|
| | DAS, Milk Base Activity | | | DAS, Whey Base Activity | | |
| | pH | 1% only | cfu/ml | pH | 1% only | cfu/ml |
| No holdover | 5.75 | 0.89 | $9.0 \times 10^8$ | 5.79 | 0.92 | $6.3 \times 10^8$ |
| 1 day, 5° C. | 5.14 | 0.84 | $6.9 \times 10^8$ | 5.23 | 0.83 | $6.1 \times 10^8$ |
| 1 day, 25° C. | 4.85 | 0.70 | $9.8 \times 10^8$ | 4.82 | 0.82 | $1.2 \times 10^9$ |
| 3 days, 5° C. | 5.10 | 0.83 | $7.5 \times 10^8$ | 5.15 | 0.79 | $9.0 \times 10^8$ |
| 3 days, 25° C. | 4.87 | 0.09 | $1.4 \times 10^8$ | 4.84 | 0.10 | $7.5 \times 10^7$ |

Activity holds up well in both media for up to three days 5° C. and 1 day at 25° C., yet both media are essentially nonactive after three days at room temp. Although cultures appeared to increase in viable cell numbers during the 1 day holdover at 25° C., activity did not improve.

TABLE VI

| Holdover of Culture WP in DAS Media | | | | | | |
|---|---|---|---|---|---|---|
| | DAS, Milk Base Activity | | | DAS, Whey Base Activity | | |
| | pH | 1% only | cfu/ml | pH | 1% only | cfu/ml |
| No holdover | 5.12 | 1.02 | $9.5 \times 10^8$ | 5.13 | 1.03 | $1.2 \times 10^9$ |
| 1 day, 5° C. | 5.12 | 0.94 | $8.3 \times 10^8$ | 5.12 | 0.97 | $9.8 \times 10^8$ |
| 1 day, 25° C. | 4.99 | 0.60 | $1.2 \times 10^9$ | 4.96 | 0.61 | $8.7 \times 10^8$ |
| 3 days, 5° C. | 5.10 | 0.81 | $1.1 \times 10^9$ | 5.11 | 0.74 | $8.5 \times 10^8$ |
| 3 days, 25° C. | 4.99 | 0.06 | $6.3 \times 10^7$ | 4.95 | 0.05 | $1.6 \times 10^8$ |
| 10 days, 5° C. | 5.32 | 0.35 | $1.0 \times 10^9$ | 5.12 | 0.31 | $8.4 \times 10^8$ |
| 10 days, 25° C. | 5.00 | 0.00 | $<10^7$ | 4.97 | 0.00 | $<10^7$ |

Some activity remains with both media up to 10 days at 5° C., whereas almost none remains after 3 days at 25° C., and a substantial decrease is seen after 1 day at 25° C. The results with WP are perhaps more representative than those with MFS, since the "break" pH of the media is commonly closer to 5.12 than to 5.75.

EXAMPLE 6

A growth medium was prepared by mixing 29 g of whey powder with 4 g of yeast extract, 12 g of DAS, 10 g of DAP, 4 g of sodium citrate dihydrate, and 1 g of $Mg_3(PO_4)_2 \cdot 8H_2O$. A second medium was prepared in which 29 g of nonfat milk (NFM) powder replaced the 29 g of whey powder in the formulation above. Both media were heated to and held at 85° C. for 45 min with agitation, then cooled to 25° C. and inoculated with 0.5 ml of a freshly thawed Hansen's commercial starter #57. The media were agitated the first and last 15 min of growth only. Activity and viable cell numbers were measured after 16¼ hr of growth at 25° C., as described in Example 1; results are shown in Table VII.

TABLE VII

|  | DAS w/Whey | DAS w/NFM |
|---|---|---|
| Activity, 16 hr | 2.7 | 2.7 |
| cfu/ml, 16 hr | $3.1 \times 10^9$ | $3.0 \times 10^9$ |

Thus, addition of sodium citrate has no apparent adverse effect on starter growth in the DAS medium, and NFM may be used in place of whey (1:1 ratio) without affecting cell growth or activity.

EXAMPLE 7

A growth medium was prepared by mixing 28 g of nonfat milk powder with 4 g of yeast extract, 1 g of $Mg_3(PO_4)_2.8H_2O$, 12 g of DAS, 15 g of DAP, and 4 g of citric acid, monohydrate, then suspending this mixture in 800 ml of water. The medium was pasteurized with agitation for 45 min at 85° C., then cooled to 25° C. and inoculated with 0.5 ml of one of the following freshly thawed commercial starter cultures: Hansen's #91, #82, #101, #70, #253, #102, #44, #99, #56, #60, #98, #96, or #82; or Marschall's SG1, OS, SLA, HAZ, LD, MFS, OD, MRD, WP, CJB, VT6, MD, CS28, or KH. Fermentation continued for 16¼ hrs at 25° C., with agitation used only during first and last 15 min of growth. Following the fermentation, the media were sampled for activity in 11% (w/w) pasteurized nonfat milk at 0.5%, 1.0%, and 2.0%, using the activity test described in Example 1. Viable cell counts after 16¼ hr of growth in each medium were made using a drop-plate technique on M17 agar, the plates then incubated at 30° C. aerobically for 36 hr. The results are summarized in attached Table VIII.

TABLE VIII

| Culture | Activity[a] | | |
|---|---|---|---|
| | 0.5% | 1.0% | 2.0% |
| 91 | 0.45 | 0.65 | 0.86 |
| 82 | 0.44 | 0.76 | 1.05 |
| 101 | 0.25 | 0.46 | 0.91 |
| 70 | 0.46 | 0.80 | 1.13 |
| 253 | 0.53 | 0.79 | 1.08 |
| 102 | 0.74 | 1.06 | 1.37 |
| 44 | 0.56 | 0.88 | 1.26 |
| 99 | 0.59 | 0.88 | 1.22 |
| 56 | 0.64 | 0.98 | 1.29 |
| 60 | 0.63 | 0.94 | 1.17 |
| 98 | 0.62 | 0.95 | 1.25 |
| 96 | 0.64 | 1.01 | 1.30 |
| 82 | 0.43 | 0.74 | 1.06 |
| SG1 | 0.77 | 1.06 | 0.32 |
| OS | 0.67 | 1.02 | 1.31 |
| SLA | 0.62 | 0.97 | 1.26 |
| HAZ | 0.84 | 1.14 | 1.40 |
| LD | 0.54 | 0.77 | 1.01 |
| MFS | 0.62 | 0.92 | 1.18 |
| OD | 0.54 | 0.87 | 1.19 |
| MRD | 0.67 | 1.02 | 1.37 |
| WP | 0.77 | 1.03 | 1.28 |
| CJB | 0.49 | 0.78 | 1.06 |
| VT6 | 0.60 | 0.89 | 1.10 |
| MD | 0.65 | 0.94 | 1.14 |
| CS28 | 0.38 | 0.58 | 0.85 |
| KH | 0.45 | 0.68 | 1.05 |

[a]Activity is presented as the change in the pH of milk after four hours following inoculation with 0.5%, 1.0%, or 2.0% of mature starter culture cells grown for 16¼ hr in the appropriate bulk starter medium.

The relative lack of variability between the activities of cultures grown with different starters shows the broad usefulness of the medium. This lack of variability is also of great value to the cheesemake since it confers a high degree of predictability about activity.

EXAMPLE 8

A growth medium was prepared by mixing 28 g of whey powder with 4 g of yeast extract, 0.42 g of $Mg(OH)_2$, 16 g of DAP, and 4.63 g of citric acid monohydrate, then suspending this mixture in 800 ml of water. Two additional media were prepared by adding 6 g of DAA or 12 g of DAS to the ingredients above. All media were pasteurized with agitation at 85° C.; for 45 min, then cooled to 25° C. and inoculated with 1% by volume of S. cremoris HP. Agitation was used only during the first and last 15 min of growth. Activity and viable cell numbers were measured as described in Example 1 after 16¼ hr of fermentation at 25° C.; results are given in Table IX, including initial and final pH of media.

TABLE IX

| | Basal Medium | DAS Medium | DAA Medium |
|---|---|---|---|
| Activity, 16¼ hr | 2.6 | 2.4 | 2.4 |
| cfu/ml, 16¼ hr | $5.0 \times 10^9$ | $3.8 \times 10^9$ | $3.4 \times 10^9$ |
| pH, 0 hr | 6.78 | 6.60 | 6.77 |
| pH, 16 hr | 4.76 | 5.19 | 5.15 |

The lack of either buffer (DAS or DAA) in the basal medium allows the pH to fall below 5.0, which is undesirable since cells will maintain activity for only a few hours under these conditions.

EXAMPLE 9

A basal medium was prepared as in Example 8 containing 28 g of whey powder, 4 g of yeast extract, 0.42 g of $Mg(OH)_2$, 16 g of DAP, and 4.63 g of citric acid monohydrate in 800 ml of water. Six different media were derived from this basal blend by adding (A) 12 g of DAS, (B) 12 g of DAA, (C) 10 g of DAA, (D) 8 g of DAA, (E) 6 g of DAA, or (F) 4 g of DAA. All media wee pasteurized at 85° C. for 45 min with agitation, cooled to 25° C., and inoculated with 1% by volume of S. cremoris HP. Agitation was continued during first and last 15 min of growth only. Following a 16¼ hr fermentation at 25° C., activity and viable cell numbers were measured as described in Example 1. The pH of each medium before and after culture growth was also recorded. Results are given in Table X.

TABLE X

| Media | pH, 0 hr | pH, 16 hr | pH, 20 hr | Activity 16¼ hr | cfu/ml 16¼ hr |
|---|---|---|---|---|---|
| Base + 12 g DAS | 6.59 | 5.04 | 5.00 | 3.0 | $3.2 \times 10^9$ |
| + 12 g DAA | 6.72 | 5.38 | 5.30 | 2.7 | $2.8 \times 10^9$ |
| + 10 g DAA | 6.72 | 5.31 | 5.24 | 2.9 | $2.4 \times 10^9$ |
| + 8 g DAA | 6.72 | 5.21 | 5.15 | 2.8 | $3.9 \times 10^9$ |
| + 6 g DAA | 6.71 | 5.11 | 5.05 | 2.9 | $3.1 \times 10^9$ |
| + 4 g DAA | 6.70 | 4.98 | 4.93 | 2.9 | $3.0 \times 10^9$ |

The above data show that DAA holds the pH of the medium after growth at a higher level than would be expected from buffering alone, and that this effect may be due to an inhibition (regulation) of the growth rate of the starter culture. Thus, 5-6 g of DAA is equivalent in apparent buffering or growth regulation effectiveness to 12 g of DAS.

EXAMPLE 10

A growth medium was prepared as in Examples 8 and 9 by mixing 28 g of whey powder with 4 g of yeast extract, 16 g of DAP, 12 g of DAS, 0.42 g of $Mg(OH)_2$, and 4.63 g of citric acid monohydrate, and suspending this mixture in 800 ml of water. A second medium was prepared in which the 12 g of DAS in the blend above was replaced by 6 g of DAA. Both media were pasteurized at 85° C. with agitation for 45 min, then cooled to 25° C. and inoculated with 0.5 ml of one of the following freshly-thawed commercial starter cultures Marschall's M13, M21, or SG1; or Hansen's #60, #98, or

102. The pH of each medium was measured before and after fermentation; activity and viable cell numbers were measured as described in Example 1 after a 16¼ hr fermentation at 25° C. The media were agitated for only the first and last 15 min of culture growth. Results are summarized in Table XI.

TABLE XI

|  | DAS Medium | | | DAA Medium | | | |
|---|---|---|---|---|---|---|---|
|  | pH | | Activity | cfu/ml | pH | | Activity | cfu/ml |
| Culture Used | 0 hr | 16 hr | 16¼ hr | 16¼ hr | 0 hr | 16 hr | 16¼ hr | 16¼ hr |
| Marschall's M13 | 6.59 | 5.23 | 2.7 | $2.4 \times 10^9$ | 6.71 | 5.24 | 2.8 | $2.0 \times 10^9$ |
| Marschall's M21 | 6.59 | 5.20 | 2.5 | $5.7 \times 10^8$ | 6.71 | 5.22 | 2.8 | $8.6 \times 10^8$ |
| Marschall's SG1 | 6.59 | 5.36 | 2.4 | $8.7 \times 10^8$ | 6.71 | 5.27 | 2.6 | $9.3 \times 10^8$ |
| Hansen's #60 | 6.50 | 5.25 | 2.6 | $9.7 \times 10^8$ | 6.67 | 5.30 | 2.6 | $1.3 \times 10^9$ |
| Hansen's #98 | 6.49 | 5.23 | 2.4 | $5.2 \times 10^8$ | 6.67 | 5.25 | 2.5 | $7.4 \times 10^8$ |
| Hansen's #102 | 6.48 | 5.17 | 2.5 | $1.2 \times 10^8$ | 6.66 | 5.19 | 2.6 | $8.6 \times 10^8$ |

For all the cultures tested, activity and final viable cell numbers were equal or better in the DAA than in the DAS medium. Also, the final pH in both media was about equal, though the buffering capacity of the DAA medium should be lower. The mechanism of action is unclear.

EXAMPLE 11

A growth medium was prepared as in Examples 9 and 10 by mixing 28 g of whey with 16 g of DAP, 6 g of DAA, 4 g of yeast extract, 4.63 g of citric acid monohydrate, and 0.42 g of $Mg(OH)_2$, then adding this mixture to 800 ml of water. Two additional media were prepared by adding 2.8 g or 5.6 g of sodium caseinate to the above ingredients. All media were pasteurized at 85° C. for 45 min with agitation, then cooled to 25° C. and inoculated with 0.5 ml of freshly thawed Hansen's #44. Media were agitated only for the first and last 15 min of fermentation. Activity and cfu/ml of media were measured after 16¼ hr of fermentation at 25° C., as described in Example 1. pH measurements of each medium were made before and after growth. Results are given in Table XII.

TABLE XII

|  | DAA Medium | DAA + 2.8 g Casein | DAA + 5.6 g Casein |
|---|---|---|---|
| pH, 0 hr | 6.74 | 6.75 | 6.74 |
| pH, 16 hr | 5.18 | 5.18 | 5.18 |
| Activity, 16¼ hr | 1.87 | 1.91 | 1.96 |
| cfu/ml, 16¼ hr | $2.6 \times 10^9$ | $2.7 \times 10^9$ | $2.2 \times 10^9$ |

EXAMPLE 12

A growth medium (basal medium) was prepared by mixing 22 g of whey powder with 6 g of casein, 4 g of yeast extract, 0.42 g $Mg(OH)_2$, 4.63 g citric acid monohydrate, and 16 g of DAP, when suspending this mixture in 800 ml $H_2O$. Two additional media were prepared, one by adding 6 g of DAA to the above mixture, a second by adding 12 g of DAS. All media were pasteurized with agitation for 45 min at 85° C., cooled to 25° C., and inoculated with 1% of a 16 hr (21° C.) nonfat milk culture of *Streptococcus cremoris* 205. This organism is available at Oregon State University. Agitation was continued for only the first and last 15 min of growth; the fermentation continued for 16½ hr at 24° to 25° C. Following growth, each medium was tested for activity, and pH and viable cells per ml were measured as described in Example 1. Each medium was then divided into two portions. One was stored at 25° C., and a second cooled rapidly and stored at 10° C. Plate counts, pH, and activity were again measured in all four media after 24 hr and 48 hr of storage at both 10° C. and 25° C. Results are given below in Table XIII.

TABLE XIII

|  | Basal Medium | DAA Medium | DAS Medium |
|---|---|---|---|
| pH after fermentation | 4.67 | 5.03 | 5.07 |
| pH after 24 hr at 10° C. | 4.59 | 4.88 | 5.00 |
| pH after 48 hr at 10° C. | 4.68 | 4.94 | 5.05 |
| pH after 24 hr at 25° C. | 4.57 | 4.85 | 4.95 |
| pH after 48 hr at 25° C. | 4.60 | 4.88 | 5.01 |
| Activity$^a$ after fermentation | 1.55 | 1.55 | 1.52 |
| Activity$^a$ after 24 hr at 10° C. | 1.11 | 1.35 | 1.31 |
| Activity$^a$ after 48 hr at 10° C. | 0.61 | 1.29 | 1.22 |
| Activity$^a$ after 24 hr at 25° C. | 0.21 | 0.56 | 0.75 |
| Activity$^a$ after 48 hr at 25° C. | 0.14 | 0.18 | 0.22 |
| cfu/ml after fermentation | $3.0 \times 10^9$ | $2.2 \times 10^9$ | $2.2 \times 10^9$ |
| cfu/ml after 24 hr at 10° C. | $2.4 \times 10^9$ | $2.7 \times 10^9$ | $2.2 \times 10^9$ |
| cfu/ml after 48 hr at 10° C. | $2.0 \times 10^9$ | $2.0 \times 10^9$ | $2.1 \times 10^9$ |
| cfu/ml after 24 hr at 25° C. | $2.3 \times 10^9$ | $2.6 \times 10^9$ | $2.4 \times 10^9$ |
| cfu/ml after 48 hr at 25° C. | $1.1 \times 10^9$ | $1.5 \times 10^9$ | $1.4 \times 10^9$ |

$^a$Activity measured at 2% only.

None of the three test media (the basal blend, the DAA-buffered blend, or the DAS-buffered blend) retained satisfactory activity after as little as 24 hr of storage at 25° C., the weakly buffered basal blend losing its activity most rapidly. Viable cell numbers also decreased after 48 hr at 25° C.; this decrease was most dramatic in the basal blend. At 10° C., activity was retained at a satisfactory level up to 48 hr in the DAA and DAS blends, the DAA blend allowing the best retention of activity; the basal blend lost activity rapidly at 10° C. and was unacceptable after 48 hr. Viable plate counts decreased only slightly after all three blends at 10° C. during 48 hr. Results show that addition of the buffers DAA and DAS to the basal medium improve the refrigerated (10° C.) holdover of this blend, which may be of practical significance since bulk starters are sometimes held over for a day or two under field conditions.

EXAMPLE 13

A growth medium was prepared by mixing 22 g of whey powder with 6 g of casein, 16 g of DAP, 4 g of yeast extract, 4.63 g of citric acid monohydrate, 0.42 g of $Mg(OH)_2$, and 52 g of Maltrin M050 (Grain Processing Corp., Muscatine, Iowa), then adding this mixture to 800 ml of water. Two additional media were prepared: (A) the above ingredients with 6 g of DAS added and the Maltrin reduced to 46 g, and (B) the above ingredients with 12 g of DAS added and the Maltrin reduced to 40 g. All media were pasteurized at 85° C. for 45 min with agitation, then cooled to 25° C. and inoculated with 0.5 ml of freshly thawed Marschalls M21 commercial starter. All media were agitated for the first and last 15 min of fermentation. Starter growth continued for 16¼ hr at 25° C., then the media were sampled for activity and viable cell counts (see Example 1) and cooled to 10° C. Media were again sampled for activity, cell counts, and PH after 1, 2, 3, and 6 days at 10° C. Results are summarized in Table XIV.

TABLE XIV

|  | Basal Medium | | | DAA Medium | | | DAS Medium | | |
| --- | --- | --- | --- | --- | --- | --- | --- | --- | --- |
|  | pH | cfu/ml | Activity[a] | pH | cfu/ml | Activity[a] | pH | cfu/ml | Activity[a] |
| No holdover | 4.80 | $1.9 \times 10^9$ | 3.3 | 5.20 | $1.6 \times 10^9$ | 3.3 | 5.18 | $1.3 \times 10^9$ | 3.3 |
| 1 day, 10° C. | 4.68 | $2.1 \times 10^9$ | 3.5 | 5.03 | $2.2 \times 10^9$ | 3.6 | 5.13 | $2.3 \times 10^9$ | 3.5 |
| 2 days, 10° C. | 4.70 | $2.3 \times 10^9$ | 3.3 | 4.99 | $2.1 \times 10^9$ | 3.6 | 5.13 | $2.1 \times 10^9$ | 3.1 |
| 3 days, 10° C. | 4.66 | $1.9 \times 10^9$ | 2.9 | 4.96 | $1.9 \times 10^9$ | 3.4 | 5.09 | $1.1 \times 10^9$ | 3.1 |
| 6 days, 10° C. | 4.70 | $7.6 \times 10^8$ | 0.9 | 5.00 | $1.3 \times 10^9$ | 2.2 | 5.13 | $3.3 \times 10^8$ | 1.6 |

[a]Activity test used was 30° C. for 5 hr; activity was then calculated as described in Example 1.

The medium containing DAA retained good activity and cell counts out to 6 days. The DAS medium was still useable, although marginal. Basal medium without either buffer had fallen markedly in activity at 6 days.

EXAMPLE 14

It was demonstrated that alkali metal and ammonium salts and double salts of straight chain aliphatic dibasic acids can be used successfully in a phage inhibitory growth medium by mixing 29 g of whey powder with 4 g of yeast extract, 12 g of DAS, and 10 g of DAP, then suspending this mixture in 800 ml of water, heating wih agitation to 85° C., holding at this temperature for 45 minutes, and then cooling to 25° C. Two vessels of this medium were prepared: one was inoculated with a lactic acid-producing organism Streptococcus cremoris 205 at 1% by volume (or approximately $10^5$ viable cells per ml of medium), a second was inoculated with S. cremoris 205 at 1% plus $10^5$ plaque-forming units per ml of medium of the homologous phage T189. These bacterial and phage cultures are available at Oregon State University. Agitation was continued for three hours after inoculation, then discontinued until 15 min prior to sampling; total fermentation time was 16 hr. Activity, viable cell numbers (cfu/ml) and plaque-forming units (pfu/ml) resulting after fermentation are given in Table XIV. Plaque-forming units were also counted on M17 agar using a single overlay technique and 24 hr of incubation at 30° C.

TABLE XV

|  | Vessel A (S. cremoris 205 only) | Vessel B (S. cremoris 205 + phage T189) |
| --- | --- | --- |
| cfu/ml at 16 hr | $1.7 \times 10^9$ | $1.9 \times 10^9$ |
| Activity at 16 hr | 2.6 | 2.5 |
| pfu/ml at 16 hr | none | $1.6 \times 10^3$ |

The experimental DAS-containing medium is phage-inhibitory, resulting in a decrease (98%) in phage titer from $1 \times 10^5$ pfu/ml to $1.6 \times 10^3$ pfu/ml after a 16 hr (25° C.) fermentation in the presence of a homologous host while the host cells grow to large numbers and remain active.

EXAMPLE 15

A growth medium was prepared as in Examples 1 and 2 by mixing 29 g of whey powder with 4 g of yeast extract, 12 g of DAS, and 10 g of DAP, then suspending this mixture in 800 ml of water. A second medium was prepared containing 1.0 g of $Mg_3(PO_4)_2$ in addition to the above ingredients. The media were heated to and held at 85° C. for 45 min with agitation, then cooled to 25° C. and inoculated with 1% by volume of Streptococcus cremoris 205, resulting in about $10^5$ cfu/ml of medium. A second vessel of each medium was inoculated with 1% of S. cremoris 205 plus $10^5$ pfu/ml of the homologous phage T189. The media were agitated only during the first and last 15 min of growth, except as indicated on the footnote. Activity, viable cell numbers, and pfu/ml after 16¼ hr of fermentation are given in Table XVI. All were measured as described in Examples 1 and 14.

TABLE XVI

|  | DAS[a] | | DAS + $Mg_3(PO_4)_2$[b] | |
| --- | --- | --- | --- | --- |
|  | with phage | w/o phage | with phage | w/o phage |
| Activity, 16¼ hr | 2.5 | 2.6 | 0.3 | 2.3 |
| cfu/ml 16¼ hr | $1.9 \times 10^9$ | $1.7 \times 10^9$ | $1.3 \times 10^8$ | $2.4 \times 10^9$ |
| pfu/ml, 0 hr | $10^5$ | none | $10^5$ | none |
| pfu/ml, 16¼ hr | $1.6 \times 10^3$ | none | $4.3 \times 10^8$ | none |

[a]Agitated first 3 hr and last 15 min.
[b]Agitated first and last 15 min.

Addition of $Mg_3(PO_4)_2$ results in loss of phage protection in the DAS medium. Note that addition of $Mg_3(PO_4)_2$ did not improve growth of S. cremoris as compared with commercial starter media.

EXAMPLE 16

A growth medium was prepared by mixing 22 g of whey, 6 g of casein, 16 g of DAP, 6 g of DAA, 4 g of yeast extract, 0.42 g of $Mg(OH)_2$, and 4.63 g of citric acid monohydrate, then adding this mixture to 800 ml of $H_2O$. This was pasteurized at 85° C. for 45 min with agitation, then cooled to 24° C. One vessel of the medium was inoculated with 1% of S. cremoris 205; a second vessel was inoculated with 1% of S. cremoris 205 (host) plus approximately $10^5$ plaque forming units per ml of phage T189 (homologous phage). Agitation occurred during the first and last 15 min of the 17 hr fermentation. Viable cell numbers, activity, and plaque-forming units were measured after growth as previously described; results are given in Table XVII.

TABLE XVII

|  | DAA Medium | |
| --- | --- | --- |
|  | No Phage | With Phage |
| cfu/ml at 17 hr | $2.4 \times 10^9$ | $2.3 \times 10^9$ |
| pfu/ml at 17 hr | — | $1.9 \times 10^5$ |
| Activity at 17 hr | 2.64 | 2.55 |

Despite the initial phage infection, the medium retained excellent activity and a high bacteria population.

EXAMPLE 17

The dicarboxylic acid salts of the present invention are highly effective buffers to prevent pH drop due to bacterially generated lactic acid. In order to show buffering capacity, the following formulations were made up in 800 ml of water.

TABLE XVIII

| Sample No. | 1 | 2 | 3 | 4 | 5 | 6 |
|---|---|---|---|---|---|---|
| Dried Whey, g | 28 | same | same | same | same | same |
| Yeast Extract, g | 4 | same | same | same | same | same |
| $(Mg)_3(PO_4)_2$, g | 1 | — | — | — | — | — |
| Ingred. Blend*, g | — | 1 | same | same | same | same |
| DAP, g | 15 | 16 | same | same | same | same |
| Citric Acid $H_2O$, g | 4 | same | same | same | same | same |
| DAS, g | 12 | 12 | — | — | — | — |
| DAA, g | — | — | 20 | 17.5 | 14 | 12 |

*Ingred. Blend is a mixture of 58.3% citric acid and 41.7% Mg(OH)$_2$. The blend is manufactured according to the process of U.S. Patent Application S.N. 450,979.

After stirring each medium, they were titrated with 85% lactic acid/15% lactic anhydride solution in indicated increments down to pH 4.5. The pH after each incremental addition was recorded.

TABLE XIX

| ml Lactic Acid Solution | Sample pH | | | | | |
|---|---|---|---|---|---|---|
|  | 1 | 2 | 3 | 4 | 5 | 6 |
| 0 | 6.40 | 6.39 | 6.55 | 6.65 | 6.59 | 6.60 |
| 2 | 6.20 | 6.20 | 6.45 | 6.35 | 6.35 | 6.40 |
| 5 | 5.90 | 5.90 | 6.05 | 6.05 | 6.05 | 6.05 |
| 8 | 5.60 | 5.65 | 5.75 | 5.75 | 5.80 | 5.70 |
| 10 | 5.45 | 5.48 | 5.60 | 5.52 | 5.60 | 5.48 |
| 13 | 5.20 | 5.25 | 5.45 | 5.28 | 5.35 | 5.21 |
| 15 | 5.05 | 5.05 | 5.25 | 5.15 | 5.20 | 5.05 |
| 17 | 4.90 | 4.95 | 5.15 | 5.00 | 5.08 | — |
| 18 | 4.85 | — | — | — | — | 4.85 |
| 20 | 4.75 | 4.85 | 5.00 | 4.85 | 4.90 | 4.75 |
| 22 | 4.62 | 4.60 | 4.90 | 4.75 | 4.80 | 4.65 |
| 24 | 4.52 | 4.52 | 4.85 | 4.65 | 4.71 | 4.55 |
| 26 | 25.3* | 25.8* | 4.76 | 4.60 | 4.65 | 25.0* |
| 28 |  |  | 4.68 | 28.1* | — |  |
| 30 |  |  | 4.63 |  | 30.3 |  |
| 32 |  |  | 4.60 |  |  |  |
| 34 |  |  | 4.52 |  |  |  |
| 36 |  |  | 34.5* |  |  |  |

*ml lactic acid solution at pH 4.5 endpoint.

Equal weights of DAS and DAA appear to have essentially the same capacity to buffer lactic acid. DAA may be somewhat advantageous since its initial pH is slightly higher, giving a more favorable environment for bacteria growth.

EXAMPLE 18

A starter growth medium was blended for use in growing lactic streptococcal starter bacteria for use in manufacturing Cheddar cheese on a commercial scale. The medium composition per 50 gallons (417 pounds) of water was as follows:

| Grade A Sweet Whey | 5.21 kg |
|---|---|
| Casein | 1.43 |
| Yeast Extract | 0.95 |
| Ingred. Blend | 0.24 |
| Diammonium Phosphate | 3.78 |
| Citric Acid (Anhydrous) | 0.87 |
| Diammonium Adipate | 1.42 |
|  | 13.90 |
| Water | 189.15 |
| Total | 203.05 kg at 6.9% Solids |

*Ingred. Blend is a blend of starter media ingredients that comprise 58.3% citric acid and 41.7% Mg(OH)$_2$.

Dry ingredients were reconstituted into water and allowed to mix for 15 min and then pasteurized at 85° C. for 45 min. The medium was cooled to 23° C. and inoculated with 12 ml of Marschall's OS 300 gallon bulk set culture. The mixer was turned on for 15 min, and then shut off during the remainder of the incubation period. After a pH of 5.15 was attained, four 5-gallon sanitized pail amounts were removed after 10 min of mixing and immersed in an ice bath. It took approximately 3 hours 20 minutes to cool the starter to 7.2° C., and the pH dropped to 5.05 during this time. A sample was removed and checked for activity via the 4-hour activity test at 32° C., after which the grown starter was taken to a commercial cheese plant and used to make Cheddar cheese the following day. Two different commercially available starters were used as controls. The pH of the starter dropped to 5.0 on the day of cheese production after storage in a cooler at 50°-55° F.

| Reconstituting pH = | 6.51 |
|---|---|
| Titratable acidity = | 0.93 |
| Set Temperature = | 23.3° C. |
| Culture used and amount = | 12 ml of Marschall's OS |
| Final pH = | 5.05 after cooling |
| Final TA = | 2.00 after cooling |
| Incubation Time = | 13 hrs 10 min before cooling |
| 4 Hr Activity Test @ 32° C., 1% Innoculum | |
| Medium | Activity |
| Example 18 | 1.28 |
| Commercial Starter (Control A) | 1.53 |
| Commercial Starter (Control B) | .99 |

Approximately 120 lbs (0.86%) of day-old starter was added to 14,000 lbs of milk. A ripening period of 1¼ hrs at a temperature of 31°-32° C. was used prior to rennet addition.

Acid development was comparable to that of the more active commercial starter, with a pack acid of 0.27 (pH=5.9) and a mill acid of 0.77 (pH=5.18), in the preferred range for milling. The make time was also about the same as with the more active commercial starter, with a total time from addition to starter to milling of 4 hr 55 min.

The curd had a good body and texture.

When this cheese (Vat C) was about 13 days old, it was graded in comparison to two other vats made the same day but using the more active commercially available starter medium. Results were as follows:

TABLE XX

| Vat[a] | Starter | Moisture % | pH | Grade[b] |
|---|---|---|---|---|
| A | Commercial Starter A | 37.2 | 5.26 | State |
| B | Commercial Starter A | 37.8 | 5.15 | State |
| C | Example 18 | 36.9 | 5.05 | State |

[a]All milled at 0.77 titratable acidity.
[b]State grade is Wisconsin best grade cheese.

EXAMPLE 19

Other cations besides ammonium and other acids besides succinic and adipic in their homologous series are effective buffering agents in starter media for cultures of acid producing bacteria. In a demonstration of buffering capacity for lactic acid, 0.0667 mol of the sodium and ammonium salts of succinic, glutaric, and adipic acids were dissolved in 800 ml of deionized water to make 0.083 molar solutions. These solutions were titrated by the addition of 0.5 ml increments of 85% lactic acid/15% lactic anhydride solution until an endpoint of pH 4.0 was reached. Diammonium and disodium phosphate solutions of equivalent concentrations were used as control samples.

TABLE XXI

| Salt | Initial pH | ml pH 7 to pH 5 | ml pH 5 to pH 4 |
|---|---|---|---|
| Ammonium succinate | 5.93 | 4.0* | 3.5 |
| Sodium succinate | 8.72 | 5.0 | 4.0 |
| Ammonium glutarate | 5.05 | — | 4.0 |
| Ammonium adipate | 4.97 | — | 4.0 |
| Sodium adipate | 7.00 | 4.0 | 3.5 |
| Diammonium phosphate | 8.08 | 4.5 | 1.0 |
| Disodium phosphate | 8.88 | 4.5 | 1.0 |

*ml of lactic acid solution to decrease initial pH to 5.0.

The five aliphatic dibasic acid salts have roughly equivalent buffering capacity below pH 5. The same is true for the two sodium salts tested above this range. All of these dibasic acid salts are much more efficient buffers below pH 5 than are either of the phosphate salts.

EXAMPLE 20

A starter medium was made as follows for studies on the effect of trace metal ions in bacterial growth:

| | |
|---|---|
| Whey solids | 13.2 g |
| Nonfat dry milk | 14.8 |
| Yeast Extract | 4.0 |
| Diammonium phosphate | 12.0 |
| Adipic Acid | 10.0 |
| Sodium carbonate (anhyd) | 6.5 |
| Total | 60.5 g |

Since salts of many dibasic acids are not readily available chemicals of commerce, an alternative procedure is to form them in situ when the starter materials are dissolved in water. Ammonium, sodium, or potassium carbonates are preferred sources of the cation. Of these, sodium carbonate is most preferred because it has higher storage stability than ammonium carbonate and is less expensive than the potassium salt. In the formulation above, only about 90% of the stoichimetric amount of the sodium carbonate was used of that required to fully neutralize the adipic acid. This results in a somewhat lower initial pH, in the range of pH 6.85-6.90. A pH in this range is more desirable for starting bacterial growth.

An inoculum was made up as follows. Frozen vials of $S.$ $cremoris$ 205 were thawed to room temperature and added to 100 ml of sterile nonfat milk (11% solids), mixed and incubated at 21° C. for 24 hrs. These cultures were then used to inoculate pasteurized starter media.

Starter cultures were prepared by placing 850 ml of deionized water in each glass vessel of a Hanson Model 2256 Dissolution Apparatus (Hansen Research Corporation, Northridge, Calif.). Metal salts ($FeSO_4.7H_2O$, $MnCl_2.4H_2O$, or $MgSO_4.7H_2O$) were added as 1% solutions in amounts sufficient to give the desired amount of metal ions for the individual tests. The entire 60.5 g of the starter mixture was then added prior to heating to 80°-90° C. for pasteurization for 45 mins. Evaporation during pasteurization reduced liquid volume to about 800 ml. The starter media were cooled quickly to 25° C. and aliquots were removed for measurement of pH and titratable acidity. Each vessel was then inoculated with 8 ml (1%) of the above $S.$ $cremoris$ inoculum with stirring continuing for 15 min. Incubation was continued for 16 hr at 25° C., and all vessels were again stirred for 15 min prior to sampling and use as inoculuants for activity testing in milk.

Activity tests were carried out in triplicate in test tubes containing 10 ml pasteurized nonfat milk (11% solids). The test tubes were inoculated with 1% and 2% of the starter mixture just described. One set of samples was maintained at 0° C. for measurement of initial pH and titratable acidity (TA). Another set was incubated at 30° C. for 4 hrs, chilled to 0° C., and used for measurement of final pH and titratable acidity. Titratable acidity was measured using 0.1N NaOH to a phenolphthalein endpoint and expressed as $\Delta TA = (\%$ TA after incubation - % TA before incubation) Change of pH is expressed: $\Delta pH = pH$ initial - pH final.

Activity relates the change in pH to a linear change in the amount of free acid produced during incubation and is calculated:

$$\text{Activity} = \frac{H^+ \text{ final}}{H^+ \text{ initial}} = 10 \Delta pH$$

Ferrous ion was added to one set of samples in amounts of 0, 6, 8, 10, and 15 ppm of the aqueous starter medium. Manganous ion was added to a second set of samples in amounts of 0, 6, 8, 10, 15, and 20 ppm of the medium. Magnesium ion was added to a third set at 0, 10, 20, 30, 40, and 50 ppm. All initial pH values in the starter media were in the narrow range of 6.85-6.90. Results of tests on starter media are given in Table XXII. Results of activity tests in milk are given in Table XXIII.

TABLE XXII

| Cation & Usage | | Starter Media Tests | |
|---|---|---|---|
| | | Δ pH | Δ TA % |
| $Fe^{++}$ | 0 ppm | 1.25 | 0.843 |
| | 6 | 1.55 | 1.000 |
| | 8 | 1.57 | 1.009 |
| | 10 | 1.60 | 1.059 |
| | 15 | 1.60 | 1.049 |
| $Mn^{++}$ | 0 ppm | 1.30 | 0.814 |
| | 6 | 1.55 | 0.992 |
| | 8 | 1.50 | 0.972 |
| | 10 | 1.55 | 1.012 |
| | 15 | 1.50 | 0.962 |
| | 20 | 1.55 | 0.982 |
| $Mg^{++}$ | 0 ppm | 1.35 | 0.833 |
| | 10 | 1.40 | 0.903 |
| | 20 | 1.43 | 0.923 |
| | 30 | 1.47 | 0.942 |
| | 40 | 1.50 | 0.972 |
| | 50 | 1.55 | 1.022 |

TABLE XXIII

| Cation and Usage | | Activity Tests on Milk | | | | | |
|---|---|---|---|---|---|---|---|
| | | 1% Inoculum | | | 2% Inoculum | | |
| | | Δ TA, % | Δ pH | Activity | Δ TA, % | Δ pH | Activity |
| $Fe^{++}$ | 0 ppm | 0.078 | 0.38 | 2.37 | 0.122 | 0.50 | 3.16 |
| | 6 | 0.137 | 0.55 | 3.55 | 0.197 | 0.80 | 6.31 |
| | 8 | 0.157 | 0.65 | 4.47 | 0.211 | 0.85 | 7.08 |
| | 10 | 0.157 | 0.65 | 4.47 | 0.215 | 0.85 | 7.08 |
| | 15 | 0.132 | 0.58 | 3.76 | 0.215 | 0.88 | 7.50 |
| $Mn^{++}$ | 0 ppm | 0.080 | 0.40 | 2.51 | 0.109 | 0.50 | 3.16 |

TABLE XXIII-continued

| Cation and Usage | | Activity Tests on Milk | | | | | |
|---|---|---|---|---|---|---|---|
| | | 1% Inoculum | | | 2% Inoculum | | |
| | | Δ TA, % | Δ pH | Activity | Δ TA, % | Δ pH | Activity |
| | 6 | 0.129 | 0.60 | 3.98 | 0.199 | 0.80 | 6.31 |
| | 8 | 0.119 | 0.55 | 3.55 | 0.204 | 0.80 | 6.31 |
| | 10 | 0.134 | 0.55 | 3.55 | 0.209 | 0.80 | 6.31 |
| | 15 | 0.129 | 0.58 | 3.76 | 0.204 | 0.80 | 6.31 |
| | 20 | 0.119 | 0.55 | 3.55 | 0.199 | 0.80 | 6.31 |
| $Mg^{++}$ | 0 ppm | 0.070 | 0.40 | 2.51 | 0.109 | 0.50 | 3.16 |
| | 10 | 0.080 | 0.38 | 2.37 | 0.124 | 0.55 | 3.55 |
| | 20 | 0.100 | 0.45 | 2.82 | 0.139 | 0.60 | 3.98 |
| | 30 | 0.095 | 0.48 | 2.99 | 0.139 | 0.63 | 4.22 |
| | 40 | 0.100 | 0.50 | 3.16 | 0.154 | 0.68 | 4.73 |
| | 50 | 0.105 | 0.55 | 3.55 | 0.179 | 0.75 | 5.62 |

It appears that trace amounts (<100 ppm) of the three metals tested above added to the starter medium produce bacteria that are more active than those in starter media without the trace metals. Further tests made using cuprous, chromic, and molyblenum$^{6+}$ ions showed none of them to be as effective as the three reported earlier in this example when used under similar test conditions.

Although insoluble materials would exist in such a medium if more than about 50 ppm of magnesium were present, such insoluble material would be very low, i.e. insufficient, to create a need for agitation during fermentation.

EXAMPLE 21

Combinations of ferrous iron (10 ppm) and manganous ion (5 ppm) produced activities somewhat greater than either $Fe_{++}$, $Mn_{++}$, or $Mg_{++}$ alone. The combination of $Fe^{++}$ (10 ppm), $Mn^{++}$ (5 ppm) and $Mg^{++}$ (50 ppm) was about equivalent to the combination of ferrous and manganous ions by themselves. Results are shown in Table XXIV. Procedures used were those described in Example 20.

TABLE XXIV

| Cation and Usage | | | Activity Tests on Milk | | | | | |
|---|---|---|---|---|---|---|---|---|
| | | | 1% Inoculum | | | 2% Inoculum | | |
| | | | Δ TA, % | Δ pH | Activity | Δ TA, % | Δ pH | Activity |
| None | | | 0.090 | 0.38 | 2.37 | 0.114 | 0.50 | 3.16 |
| $Fe^{++}$ | 10 ppm | | 0.144 | 0.65 | 4.47 | 0.239 | 0.83 | 6.68 |
| $Mn^{++}$ | 5 ppm | | 0.149 | 0.60 | 3.98 | 0.229 | 0.88 | 7.50 |
| $Mg^{++}$ | 50 ppm | | 0.149 | 0.60 | 3.98 | 0.239 | 0.83 | 6.68 |
| $Fe^{++}$ $Mn^{++}$ | 10 ppm and 5 ppm | | 0.159 | 0.65 | 4.47 | 0.259 | 0.90 | 7.94 |
| $Fe^{++}$ $Mn^{++}$ $Mg^{++}$ | 10 ppm 5 ppm and 50 ppm | | 0.164 | 0.70 | 5.01 | 0.259 | 0.85 | 7.08 |

EXAMPLE 22

The nonfat dried milk used in a number of previous examples represent a relatively high cost ingredient. Tests were made to see if whey or whey permeate could be used to replace part of the nonfat milk. Whey permeate is a fraction of dialyzed whey high in lactose and low in protein available from Foremost Foods, Plover, Wis. The whey used is a dried cheddar cheese whey supplied by Tillamook Creamery Association, Tillamook, Oreg. The yeast extract used in the starter media is Type YEP available from Yeast Products, Inc., Clifton, N.J. Six formulations were made as follows. Each represent an amount to be added to 800 ml of water to make a starter solution.

| Sample No. | 1 | 2 | 3 | 4 | 5 | 6 |
|---|---|---|---|---|---|---|
| Whey, g | 13.2 | — | 65.1 | — | 72.5 | — |
| Whey permeate, g | — | 13.2 | — | 65.1 | — | 72.5 |
| Nonfat dry milk, g | 14.8 | 14.8 | 7.4 | 7.4 | — | — |
| Yeast extract, g | 4.0 | same | same | same | same | same |
| DAP, g | 12.0 | same | same | same | same | same |
| Adipic Acid, g | 10.0 | same | same | same | same | same |
| $Na_2CO_3$, Anhyd, g | 6.5 | same | same | same | same | same |
| $FeSO_4 \cdot 7H_2O$, g | 0.042 | same | same | same | same | same |
| $MnCl_2 \cdot 4H_2O$, g | 0.015 | same | same | same | same | same |
| Total, g | 60.6 | 60.6 | 105 | 105 | 105 | 105 |

These mixtures were made into starter media and incoculated as described in Examples 20 and 21. They were then tested for pH drop, titratable acidity, and activity as described before.

TABLE XXV

| Medium No. | Δ pH | Δ TA, % | Solids of Starter, % |
|---|---|---|---|
| 1 | 1.60 | 1.115 | 7.0 |
| 2 | 1.60 | 1.045 | 7.0 |
| 3 | 1.45 | 1.005 | 11.6 |
| 4 | 1.45 | 1.034 | 11.6 |
| 5 | 1.45 | 1.135 | 11.6 |
| 6 | 1.45 | 1.005 | 11.6 |

TABLE XXVI

| Medium No. | Activity Tests on Milk | | | | | |
|---|---|---|---|---|---|---|
| | 1% Inoculum | | | 2% Inoculum | | |
| | Δ TA, % | Δ pH | Activity | Δ TA, % | Δ pH | Activity |
| 1 | 0.139 | 0.68 | 4.73 | 0.204 | 0.70 | 5.01 |
| 2 | 0.134 | 0.70 | 5.01 | 0.204 | 0.73 | 5.31 |
| 3 | 0.144 | 0.58 | 3.76 | 0.164 | 0.70 | 5.01 |
| 4 | 0.109 | 0.55 | 3.55 | 0.174 | 0.73 | 5.31 |
| 5 | 0.129 | 0.58 | 3.76 | 0.179 | 0.70 | 5.01 |
| 6 | 0.119 | 0.50 | 3.55 | 0.174 | 0.70 | 5.01 |

The results show that nonfat dry milk can be replaced by either whey or whey permeate.

The media described in the foregoing examples readily show that the compositions employing the novel buffering agents of the present invention produce starter cultures having high bacteria numbers and excellent activity. Activity is enhanced by the inclusion of trace amounts of ferrous and manganous ions, and also by the inclusion of manganese ions.

Having thus described the best modes known to the inventors, it will be readily apparent to those skilled in the art that many variations in the present compositions and method can be made without departing from the spirit of the invention. The invention is to be considered only as limited by the following claims.

We claim:

1. A method for preparing a food fermentation inoculum containing acid producing bacteria which comprises:
   a. providing an aqueous, liquid bacterial growth medium consisting essentially of water, essential nutrients and a dissolved, nontoxic buffering agent, wherein the buffering agent comprises buffering compounds selected from the group consisting of water soluble salts of linear aliphatic dibasic acids having from 3-6 carbon atoms and mixtures thereof, the buffering agent being present in an amount sufficient to buffer the growth medium to pH levels not less than about 5.0 for at least about 16 hours during production of a lactic acid producing strain of Streptococcus or Lactobacillus, or a mixture of such strains;
   b. inoculating the growth medium with a lactic acid producing strain of Streptococcus or Lactobacillus, or a mixture of such strains; and
   c. propagating the inoculated acid producing bacteria in the growth medium to provide food fermentation inoculum.

2. The method of claim 1 in which the buffering agent is selected from the group consisting of water soluble salts of succinic acid and mixtures thereof.

3. The method of claim 1 in which the buffering agent is selected from the group consisting of water soluble salts of adipic acid and mixtures thereof.

4. The method of claim 1 in which the buffering agent is selected from the group consisting of sodium, potassium, and ammonium salts of the acid and mixtures thereof.

5. The method of claim 1 in which the buffering agent is selected from the group consisting of diammonium succinate, glutarate, adipate, and mixtures thereof.

6. The method of claim 1 in which the buffering agent is selected from the group consisting of disodium succinate, glutarate, adipate, and mixtures thereof.

7. The method of claim 1 in which the buffering agent is selected from the group consisting of dipotassium succinate, glutarate, adipate, and mixtures thereof.

8. The method of claim 1 in which the nutrient mixture contains a nutrient material selected from the group consisting of dried whey, dried whey permeate, nonfat dried milk, and mixtures thereof.

9. The method of claim 8 in which the nutrient mixture further includes diammonium phosphate and yeast extract.

10. The method of claim 9 in which the growth medium further contains trace amounts of a metal ion selected from the group consisting of ferrous, manganous, magnesium, and mixtures thereof.

11. The method of claim 8 in which the growth medium further contains trace amounts of a metal ion selected from the group consisting of ferrous, manganous, magnesium, and mixtures thereof.

12. The method of claim 1 in which the growth medium further contains trace amounts of a metal ion selected from the group consisting of ferrous, manganous, magnesium, and mixtures thereof.

13. The method of claim 1 in which the bacteria are selected form the group consisting of *Streptococcus cremoris, S. lactis*, and mixtures thereof.

14. The method of claim 1 in which the medium contains an additional substance to enhance phage inhibition.

15. A bulk starter base suitable to form an aqueous, liquid growth medium for the propagation of acid producing bacteria to form a food fermentation inoculum, the starter base consisting essentially of:
   a. a nutrient mixture supplying essential carbohydrate and nitrogen sources; and
   b. a water soluble, nontoxic buffering agent, wherein the buffering agent is selected from the group consisting of water soluble salts of linear aliphatic dibasic acids having from 3-6 carbon atoms and mixtures thereof, the bufferinq agent being present in an amount sufficient to buffer an aqueous, liquid growth medium to pH levels not less than about 5.0 for at least about 16 hours while a lactic acid producing strain of Streptococcus or Lactobacillus, or a mixture of such strains, is propagating in the aqueous, liquid growth medium.

16. The base of claim 15 in which the buffering agent is selected from the group consisting of water soluble salts of succinic acid and mixtures of such salts.

17. The base of claim 15 in which the buffering agent is selected from the group consisting of water soluble salts of adipic acid and mixtures of such salts.

18. The base of claim 15 in which the buffering agent is selected from the group consisting of sodium, ammonium, potassium salts of the acids and mixtures of such salts.

19. The base of claim 15 in which the buffering agent is selected from the group consisting of diammonium succinate, glutarate, adipate, and mixtures thereof.

20. The base of claim 15 in which the buffering agent is selected from the group consisting of disodium succinate, glutarate, adipate, and mixtures thereof.

21. The base of claim 15 in which the buffering agent is selected from the group consisting of dipotassium succinate, glutarate, adipate, and mixtures thereof.

22. The base of claim 15 in which the nutrient mixture contains a nutrient materil selected from the group consisting of dried whey, dried whey permeate, nonfat dried milk, and mixtures thereof.

23. The base of claim 22 in which the nutrient mixture further includes a substance selected from the group consisting of diammonium phosphate, yeast extract, and mixtures thereof.

24. The base of claim 23 which further contains trace amounts of a metal ion selected from the group consisting of ferrous, manganous, magnesium and mixtures thereof.

25. The base of claim 23 which further contains trace amounts of a metal ion selected from the group of consisting of ferrous, manganous, magnesium and mixtures thereof.

26. The base of claim 15 which further contains trace amounts of a metal ion selected from the group consisting of ferrous, manganous, magnesium and mixtures thereof.

27. The base of claim 15 which contains an additional substance to enhance phage inhibition.

28. A bulk starter base suitable to form an aqueous, liquid growth medium for the propagation of acid producing bacteria to form a food fermentation inoculum, the starter base consisting essentially of:
   a. a nutrient mixture supplying essential carbohydrate and nitrogen sources; and
   b. a water soluble, nontoxic buffering agent, wherein the buffering agent comprises a source of anions selected from the group consisting of succinate, glutarate, adipate, and mixtures thereof, the buffering agent being present in an amount sufficient to buffer an aqueous, liquid growth medium to PH levels not less than abolut 5.0 for at least about 16 hours while a lactic acid producing strain of Streptococcus or Lactobacillus, or a mixture of such strains, is propagating in the aqueous, liquid growth medium.

29. An aqueous, liquid growth medium for the propagation of acid producing bacteria to form a food fermentation inoculum, the medium consisting essentially of:
   a. water;
   b. essential carbohydrate and nitrogen sources; and
   c. in solution, a water soluble nontoxic buffering agent, wherein the buffering agent comprises a source of anions selected form the group consisting of succinate, glutarate, adipate, and mixtures thereof, the buffering agent being present in an amount sufficient to buffer the medium to PH levels not less than 5.0 for at least about 16 hours while a lactic acid producing astrain of Streptococcus or Lactobacillus, or a mixture of such strains, is propagating in the medium.

* * * * *

UNITED STATES PATENT AND TRADEMARK OFFICE
CERTIFICATE OF CORRECTION

PATENT NO. : 4,766,076
DATED : August 23, 1988
INVENTOR(S) : William E. Sandine and James W. Ayres It is certified that error appears in the above-identified patent and that said Letters Patent is hereby corrected as shown below:

Claim 25, line 1, "23" should be --22--.

Signed and Sealed this

Eleventh Day of July, 1989

Attest:

DONALD J. QUIGG

*Attesting Officer*  *Commissioner of Patents and Trademarks*